(12) United States Patent
Conti et al.

(10) Patent No.: US 6,603,296 B2
(45) Date of Patent: Aug. 5, 2003

(54) APPARATUS FOR THE DETECTION AND MEASUREMENT OF PARTICULARS IN MOLTEN METAL

(75) Inventors: Richard F. Conti, Philadelphia, PA (US); William McCauley, Wynnewood, PA (US); Gregory Kopansky, Philadelphia, PA (US)

(73) Assignee: Heraeus Electro-Nite Co., Philadelphia, PA (US)

( * ) Notice: Subject to any disclaimer, the term of this patent is extended or adjusted under 35 U.S.C. 154(b) by 0 days.

(21) Appl. No.: 09/950,503

(22) Filed: Sep. 11, 2001

(65) Prior Publication Data

US 2002/0067155 A1 Jun. 6, 2002

Related U.S. Application Data

(60) Provisional application No. 60/231,783, filed on Sep. 12, 2000.

(51) Int. Cl.$^7$ ............................................... G01N 27/00
(52) U.S. Cl. ..................................................... 324/71.4
(58) Field of Search ........................ 324/71.4, 73, 717, 324/718, 724, 323–377; 377/10, 11, 12; 73/865.5; 164/4.1, 150.1; 266/78, 80, 99, 90; 204/246; 75/376, 386

(56) References Cited

U.S. PATENT DOCUMENTS

| | | | |
|---|---|---|---|
| 3,709,040 A | 1/1973 | Coe | 374/140 |
| 4,555,662 A | 11/1985 | Doutre et al. | 324/71.4 |
| 4,600,880 A | 7/1986 | Doutre et al. | 324/71.1 |
| 4,763,065 A | 8/1988 | Hachey | 324/71.4 |
| 5,039,935 A | 8/1991 | Hachey et al. | 324/71.4 |
| 5,163,997 A | * 11/1992 | Sherwood | 75/527 |
| 5,198,749 A | 3/1993 | Guthrie et al. | 324/71.1 |
| 5,241,262 A | 8/1993 | Guthrie et al. | 324/71.1 |
| 5,448,923 A | 9/1995 | Hackett | 73/864.88 |
| 5,789,910 A | 8/1998 | Guthrie | 324/71.4 |
| 5,834,928 A | 11/1998 | Doutre | 324/71.4 |

FOREIGN PATENT DOCUMENTS

| | | |
|---|---|---|
| EP | 0 398 719 A2 | 11/1990 |
| FR | 2208523 A | 6/1974 |

OTHER PUBLICATIONS

David R. Lide, Editor-in-Chief, CRC Handbook of Chemistry and Physics, 2001, CRC Press LLC, 2001–2002 82$^{nd}$ Edition, p. 4–132 and p. 12–232.*

* cited by examiner

*Primary Examiner*—N. Le
*Assistant Examiner*—John Teresinski
(74) *Attorney, Agent, or Firm*—Akin, Gump, Strauss, Hauer & Feld, L.L.P.

(57) ABSTRACT

A probe for measuring particulates in molten metal includes an inner metal receiving chamber, with an orifice to permit metal to flow into the chamber. A first electrode extends into the chamber and a second electrode surrounds at least a portion of the chamber. The electrodes are connected to a measurement device for measuring changes in the electrical potential produced by the passage of particulates entrained in the molten metal passing through the orifice. An outer sheath of heat resistant material surrounds the second electrode and a gas passageway extends out of the inner tube for creating a pressure differential within the chamber for facilitating the flow of molten metal through the orifice. A liquidus depressing material is in the chamber to lower the liquidus temperature of the molten metal and permit a longer time period for detecting and measuring particulates in the molten metal.

12 Claims, 3 Drawing Sheets

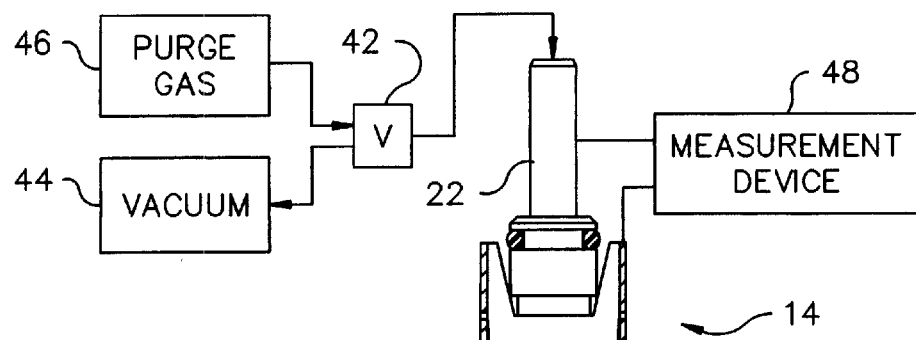
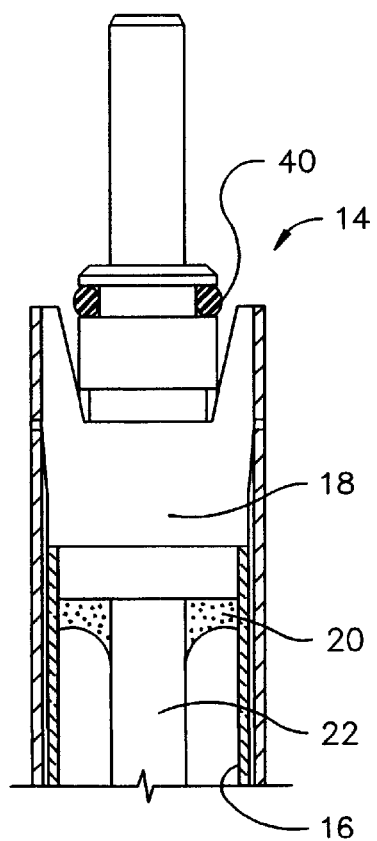
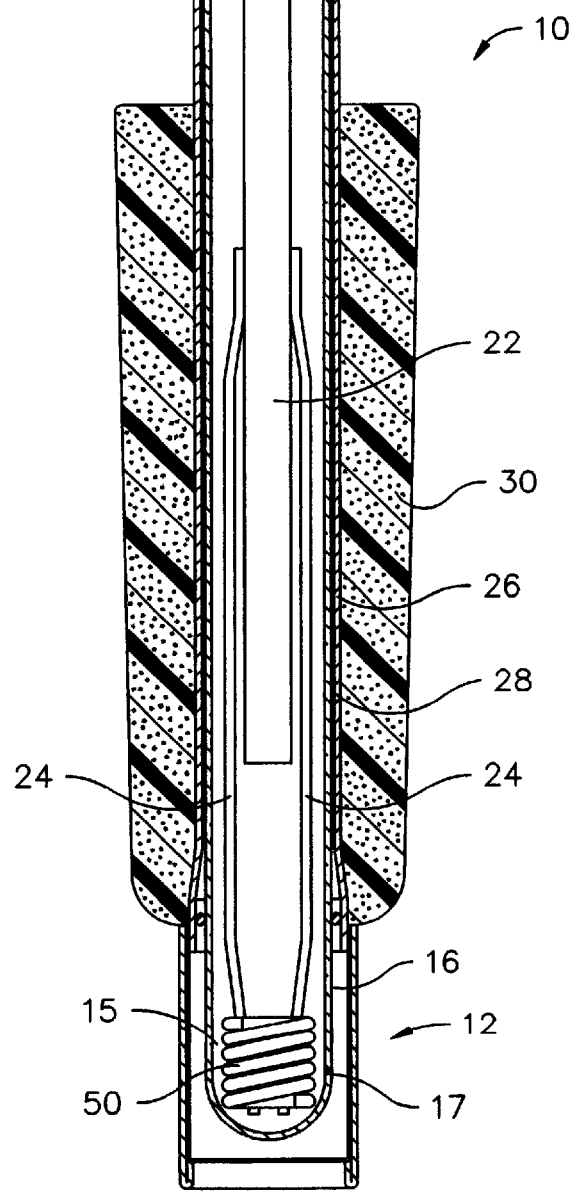
*Fig. 1*
*Fig. 2*

APPARATUS FOR THE DETECTION AND MEASUREMENT OF PARTICULARS IN MOLTEN METAL

CROSS-REFERENCE TO RELATED APPLICATIONS

The present application claims priority from U.S. Provisional Patent Application No. 60/231,783, filed Sep. 12, 2000 and entitled, "Apparatus For The Detection And Measurement Of Particulates In Molten Metal", the subject matter which is hereby incorporated herein by reference.

BACKGROUND OF THE INVENTION

The present invention relates generally to an apparatus for the detection and measurement of particulates in molten metal and, more particularly, to an improved apparatus which includes a liquidus depressing material which lowers the temperature at which sampled molten metal would normally begin to solidify, thereby, allowing for more molten metal to be sampled over a longer time period for enhanced particulate measurement.

Molten metals, particularly molten aluminum and steel, are frequently contaminated to some extent by entrained non-metallic inclusions that potentially give rise to a variety of shortcomings or defects in the resulting finished metal products. More often, a certain size or size range of non-metallic inclusions, such as alumina in deep drawing stock, is known to be harmful to the performance of the drawing stock. Knowledge of the quantity of such inclusions would be beneficial in determining the fitness for service of the finished product.

An apparatus for electrical zone sensing of suspended particles in a liquid is disclosed in U.S. Pat. No. 2,656,508 issued Oct. 20, 1953 to Wallace A. Coulter. In a typical apparatus, a tube having an aperture in its wall is positioned within a larger vessel. A liquid electrolyte suspension containing the particles to be detected and measured is placed in the vessel and is induced to flow into the tube through the aperture by establishing a fluid pressure differential between the interior of the tube and the vessel. The vessel and the tube are both fabricated of an insulator, e.g. glass, and a constant electric current is placed across the aperture. The presence of a particle in the liquid flowing through the aperture causes a change in the electrical resistance detected at the aperture and the electric voltage producing the constant current varies directly with the resistance change each time a particle passes through the aperture. A detecting circuit determines the size of the particles passing through the aperture from the change in resistivity caused by each particle, this depending upon the volume of electrolyte at the aperture displaced by the particle and by the resistivity of the kind of particles. The information is amplified and processed by suitable electronic circuits.

U.S. Pat. No. 4,555,662 describes a method and apparatus for the detection and measurement in a molten metal sample of suspended particulates of greater than a predetermined size whose electrical conductivities differ from that of the suspending molten metal. The apparatus comprises an electrically insulating vessel having a small passage (typically 200 to 500 microns in diameter) extended therethrough; a pair of electrodes disposed within and outside of the vessel to establish a current path between them through the molten metal of the sample and passing through the small passage; means for passing a sample of the molten metal through the passage; and means for passing an electric current between the two electrodes through the molten metal in the current path and for detecting a voltage change resulting from the flow of particulates through the passage. The apparatus also includes means for counting the number of voltage changes during a particular measuring period as representative of the number of particulates, and for measuring the magnitude of each of the voltage changes as representative of the size of the particulates causing the changes. The device described comprises a refractory tube with the small hole at its lower end, which is dipped into the molten metal, for example in a trough along which the molten metal is flowing. One electrode is positioned within the tube and the other outside of the tube. Molten metal is caused to pass through the small hole by means of a differential pressure applied to the tube.

The principle of operation of the apparatus described in the two above-identified patents generally refers to the measurement of non-metallic particles in molten aluminum. The devices used for the particulate measurement in molten aluminum are unsuitable for use in molten steel due to the large difference in the respective processing temperatures. The described particle counters commonly evaluate molten aluminum at a temperature of around 750° C., however, the temperature of a steel measurement would be closer to about 1550° C. Simple substitution of more suitable materials for the components of the apparatus cannot be assumed. The availability of materials which are capable of withstanding such high temperatures and are stable at such temperatures for the relatively long periods of time needed to make meaningful particulate measurements are limited as well as very expensive.

U.S. Pat. No. 5,198,749 attempts to address the numerous differences in apparatus construction due to the high processing temperature of steel and its alloys and provide a measuring strategy to overcome the difficulty of relatively long measurement times at high temperatures. The device of the '749 patent comprises a single use disposable probe that is detachably connected to a support member. The detachability of the device is common to those skilled in the art of disposable sensors for the molten iron and steel industry. The probe comprises electrode and orifice configurations of the prior more continuous devices and a jet limiting insert which serves to help cool the incoming metal immediately upon immersion of the probe into the molten metal. A meltable cover closes the orifice prior to immersion of the probe and the cover is protected by a meltable shield (slag cap) enabling the probe to be passed through an overlying slag layer without entry of slag into the probe interior. Such capping is also well known to those skilled in the art of disposable molten metal sensors. The filling of the inner chamber with the molten metal may be assisted by a reduced pressure established within the tube, or may be slowed by a positive pressure to maintain the Reynolds number of the flow below 2000. The inner chamber, is divided by a narrow bore into two compartments so that when metal enters and fills one compartment it will freeze in the bore so that it cannot enter the second compartment, protecting the vacuum source, if provided, and establishing a prescribed quantity of metal entering the probe.

Although the device of the '749 patent uses the principle of disposable, short term measurements of approximately 2 minutes to overcome the problems of long term high temperature measurements, the solution of the '749 patent has introduced a new set of problems. A short term measuring device of the above-described construction does not provide suitable time for preheating of the internal components of the probe. The entering molten metal is cast against the interior probe material that is close to room temperature and is quickly cooled. The lack of suitable preheating results in premature solidification of the molten metal entering the inner chamber effectively limiting the amount of metal which may be sampled. The liquidus temperature of a molten material is the temperature at which a solid phase begins to precipitate from the cooling liquid. The difference between the molten metal processing temperature and the liquidus temperature is called the superheat. An additional problem arises when such probes are intended for immersion in a tundish of molten steel during continuous casting. The temperature of molten steel in the tundish is generally on the order of 20–40° C. above the liquidus temperature of the steel, providing a super heat 20–40° C. The liquid steel possesses a low heat content and an inability to raise the temperature of the inner chamber walls of the probe so as to maintain a non-freezing sampling condition. The mass of the sampling apparatus itself chills the liquid metal in the chamber during filling by thermal conduction to cooler portions of the probe, thus limiting the useful application of such probes to metals having a suitable super heat.

In accordance with the present invention there is provided a molten metal inclusion sensor of the disposable type that is immersed into molten metal at a temperature near its solidification temperature, a low superheat application, and detects inclusions in the molten metal by the electric sensing zone method of the prior art. The present invention is characterized by a probe which is immersed in the molten metal for detection of the inclusions, the probe having a highly heat insulating arrangement of the inner chamber and the inner chamber containing one or more additives that effectively lower the liquidus or solidification temperature of the entering metal.

The present invention comprises an apparatus for the detection of non-conductive particulates in a bath of molten metal, specifically steel and alloys of high iron content. In use, molten metal is pumped through an orifice in an electrically insulating refractory wall to establish a current path from an inner container through the orifice to the bath of molten metal. A current is passed along the current path. Voltage changes, in the form of pulses, are measured as indicating passage of suspended particulates through the orifice. The size of the pulses provides an indication of the particle size and counting the number of pulses gives the size distribution of detected non-metallic inclusion in the molten metal.

The present invention provides a disposable apparatus for the detection and measurement of the concentration and size distribution of suspended particulates in molten metal by the electric sensing zone method that is operative relatively rapidly and has a minimum sensor mass. In one embodiment, the internal chamber electrode(s) are located along the chamber wall so that metal entering the chamber and "welling" up the thermal center of the chamber is not prematurely cooled by the electrode. As the metal fills the chamber it flows up through the thermal center then contacts the walls and electrode where it freezes and solidifies. The present invention can be employed during a processing operation on the molten metal and is capable of measuring metal close to its solidification temperature. The present invention includes an additive for decreasing the liquidus temperature of the metal in the inner chamber by alloying the entering metal with another selected metal, or selected metals chosen from several metals which are known to lower the liquidus temperature of the entering metal effectively increasing the apparent superheat and permitting a longer effective measuring time for the probe.

BRIEF SUMMARY OF THE INVENTION

Briefly stated, the present invention comprises an improved probe for insertion into molten metal to detect and measure particulates suspended therein using the electric sensing zone method. The probe comprises a generally sealed inner tube of an electrically insulated material forming a molten metal receiving chamber. The tube includes at least one orifice proximate an insertion end of the probe to permit molten metal to flow into the chamber. A first electrode extends into the chamber for engaging metal within the chamber. A second electrode surrounds at least a portion of the inner tube for engaging molten metal outside of the chamber. The first and second electrodes are connectable to a measurement device for establishing a current path through the electrodes and passing through the orifice and for measuring changes in the electrical potential between the electrodes produced by the passage of particulates entrained in the molten metal passing through the orifice. An outer sheath of heat resistant material surrounds at least a portion of the second electrode to provide thermal insulation therefore. A gas passageway extends out of the inner tube for connecting to a vacuum source to create a pressure differential between the inside and outside of the inner tube for facilitating the flow of molten metal through the orifice. The improvement comprises a liquidus depressing material installed within the chamber for alloying with molten metal entering the chamber to lower the liquidus temperature of the molten metal in the chamber and permit a longer time period for detecting and measuring particulates in the molten metal.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 1 is a cross-sectional, elevational view of a preferred embodiment of a probe in accordance with the present invention;

FIG. 2 is an enlarged cross-sectional elevational view of the connector end of the probe shown in FIG. 1;

DETAILED DESCRIPTION OF THE INVENTION

Figure 3:
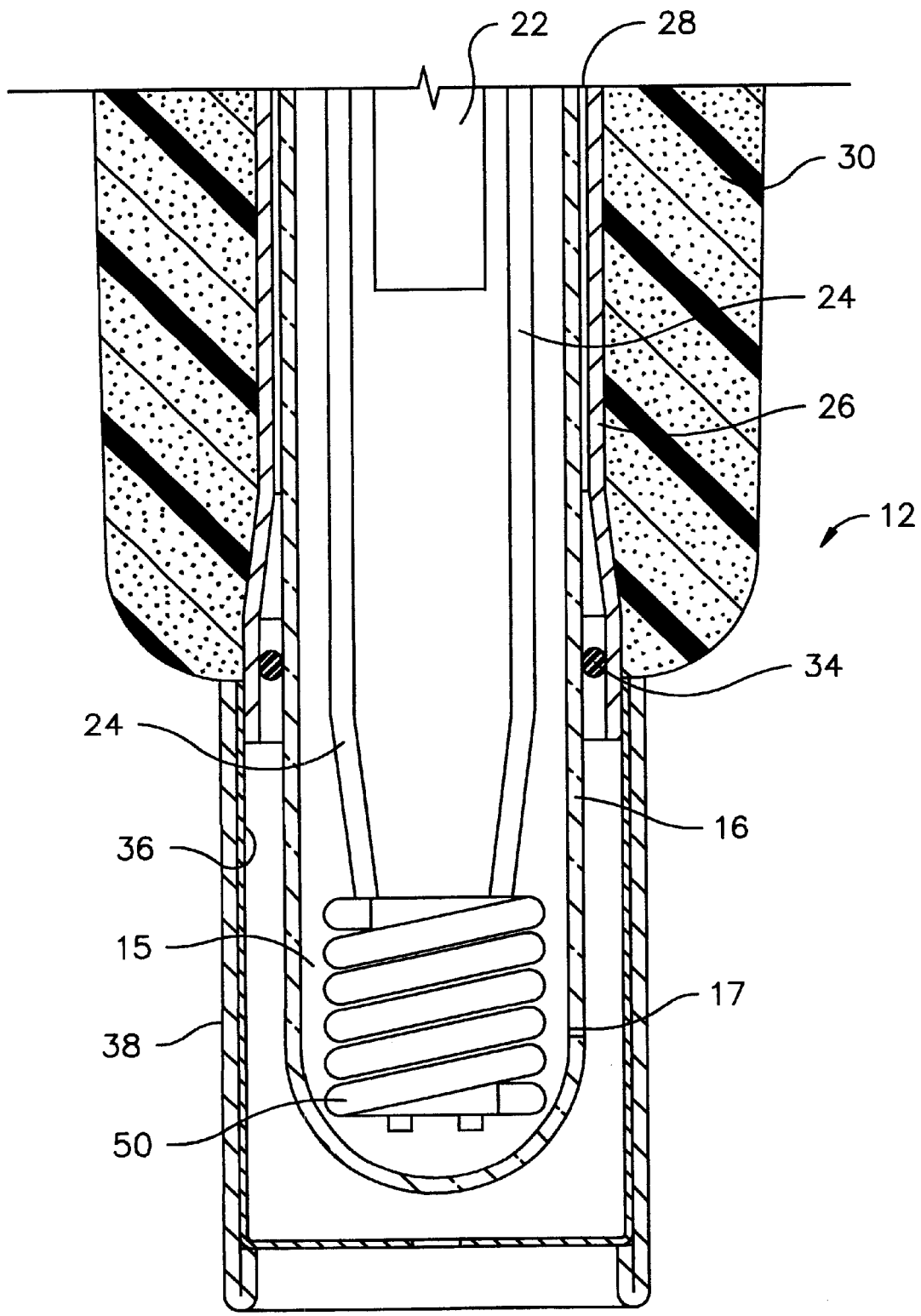
FIG. 3 is an enlarged cross-sectional elevational view of the insertion end of the probe shown in FIG. 1.

Referring to FIGS. 1–3, there is shown a preferred embodiment of a probe 10 for detecting and measuring particulates suspended in molten metal in accordance with the present invention. The probe 10 is generally elongated and cylindrical and includes an insertion end 12 and a connector end 14. The probe connector end 14 is adapted to be secured to a supporting structure (not shown) of type well known to those of ordinary skill in the art and employed for inserting measuring probes into molten metal. Further details concerning the structure and operation of the supporting structure is not necessary for a complete understanding of the present invention.

The probe 10 comprises an elongated closed end inner tube 16, which is made of an electrically insulative material capable of withstanding the high temperatures present in a bath of molten steel or other molten metal. In the present embodiment, the inner tube 16 is formed of quartz. However, it will be appreciated by those of ordinary skill in the art that other materials having the requisite electrically insulative and high temperature qualities may alternatively be employed. As shown, the insertion end of the inner tube 16 is closed and the connector end is sealed by a suitable generally cylindrical, electrically insulative plug or seal member 18. The seal member 18, which is preferably made of a polymeric material, is secured within the open end of the inner tube 16, preferably utilizing a suitable adhesive 20 to form a gas tight seal to the connector end of the inner tube 16. Although the seal member 18 is, preferably made of a polymeric material, it will be appreciated by those of ordinary skill in the art that any other suitable material capable of forming a gas tight seal with the inner tube 16 by itself or in combination with other materials, sealants, adhesives or the like may alternatively be employed. Preferably, the adhesive 20 is a commercial grade epoxy of a type suitable to formulate a seal against quartz or another material otherwise employed for forming the inner tube 16. Other adhesives known to those of ordinary skill in the art may alternatively be employed.

The insertion end of the inner tube 16 forms a molten metal receiving chamber 15. At least one orifice 17 extends through the inner tube 16 proximate to the insertion end to permit molten metal to flow into the molten metal receiving chamber 15 when the probe 10 is inserted into molten metal. The orifice 17 is preferably circular with a diameter in the range of between 300 and 1000 micrometers. It will be appreciated by those of ordinary skill in the art that the diameter of the orifice 17 could be larger or smaller, if desired and/or that the orifice 17 need not be circularly shaped. Preferably, the inner tube 16 has a wall thickness of approximately 1 mm. However, it will be appreciated by those of ordinary skill in the art that the inner tube 16 could have a thicker or thinner wall thickness, if desired. The volume of the molten metal receiving chamber 15 will vary for a particular measurement in a manner hereinafter described.

A gas passageway 22, in the present embodiment comprised of a generally cylindrical, generally tubular member, extends through the seal member 18 and into at least a portion of the inner tube 16. The gas passageway 22 is preferably formed of an electrically conductive metal, such as steel. However, other conductive materials may alternatively be employed in forming the gas passageway 22. As shown in FIGS. 1 and 3, the gas passageway 22 does not extend all the way to the insertion end of the inner tube 16.

At least one and preferably a pair of elongated generally cylindrical members 24 are secured (mechanically and electrically) to the gas passageway 22 (preferably by welding, brazing or soldering) and extend along the interior of the inner tube 16, terminating proximate to the insertion end of the inner tube 16. The elongated cylindrical members 24 are formed of an electrically conductive material and, in combination with the gas passageway 22 establish a first electrode extending into the molten metal receiving chamber 15. Preferably, the elongated cylindrical members 24 are formed of a high melting temperature electrically conductive, electrode wire of Mo, W, Fe, or some other similar high melting temperature electrically conductive material. In this manner, the first electrode effectively extends from the insertion end of the inner tube 16 to the distal end of the gas passageway 22.

The inner tube 16 is surrounded along at least a substantial portion of its length by a generally tubular, electrically conductive member 26. The tubular conductive member 26 is preferably made of steel but some other conductive material may alternatively be used. The inner dimension of the tubular member 26 is at lest slightly greater than the outer dimension of the inner tube 16 so that a small annular space 28 separates the tubular member 26 from the outer surface of the inner tube 16. At least a substantial portion of the tubular member 26 is surrounded by an outer sheath 30 formed of a heat resistant material to provide thermal insulation to the tubular member 26 when the probe 10 is inserted into molten metal. In the present embodiment, the outer sheath 30 is formed of resin coated sand which forms a phenolic bond when heated. However, it will be appreciated by the those of ordinary skill in the art that other insulative materials could alternatively be employed.

As best shown in FIG. 3, a portion of the tubular member 26 extends beyond the outer sheath 30, such that when the probe 10 is inserted into molten metal, the tubular member 26 is exposed directly to the molten metal. The other end of the tubular member 26 extends beyond the connector end of the inner tube 16, as best shown in FIG. 2. The tubular member 26 establishes a second electrode outside of the inner tube 16. The connector end of the tubular member 26 is secured to the seal member 18 by a mechanical interlock of a type well known to those of ordinary skill in the art. The interlock when engaged with the seal member 18, effectively secures together the connector end of the tubular member 26 and the connector end of the inner tube 16 allowing for an annular space 28 therebetween. A spacer 34 is inserted between the insertion end of the tubular member 26 and the inner tube 16 to maintain the annular space 28 and to prevent the insertion end of the inner tube 16 from wobbling and to help prevent breakage of the inner tube 16 during shipping and handling. Preferably, the spacer 34 comprises an O-ring formed of a suitable elastomeric material. It will be appreciated by those of ordinary skill in the art that the tubular member 26 may be secured to the inner tube 16 utilizing some other connector method and that the spacer 34 may be made of some other material.

As best shown in FIG. 3, the insertion end of the inner tube 16 is initially covered by a metal slag cap 36 and a paper cap 38. The metal slag cap 36 and the paper cap 38 protect the inner tube 16 and particularly, the orifice 17 from contamination as the probe 10 is inserted through the slag layer that typically covers molten metals during processing. The metal slag cap 16 is preferably formed of steel or some other suitable material of a type well known to those of ordinary skill in the art.

In use, the connector end 14 of the probe 10 is adapted to be temporarily connected to a suitable supporting structure (not shown) of a type well known to those of ordinary skill in the art and commonly employed for inserting measuring probes into molten metal. A seal 40 is employed for providing a gas tight connection between the gas passageway 22 and a controllable valve 42. The valve 42, in turn, is connected to a vacuum source 44 and a purge gas source 46. When the valve 42 is in a first position, the vacuum source 44 is in fluid communication through the gas passageway 22 with the inner tube 16 to thereby create a vacuum within the molten metal receiving chamber 15. The creation of a vacuum within the chamber 15, facilitates the flow of molten metal through the orifice 17 and into the chamber 15. When the valve 42 is in a second position, gas from the purge gas source 46 is supplied through the gas passageway 22 to the interior of the inner tube 16 to preclude the flow of molten metal or contaminates through the orifice 17 and into the chamber 15. The seal member 18 provides a potting area for the adhesive 20, a gas tight fitting for gas passageway 22, an attachment means for the tubular member 26 and a gasket seat for O-ring seal 40. Although such functions are performed by a single component it should be understood that multiple components could be used if desired.

When the probe 10 is connected to the supporting structure direct electrical connections are established between the connector end of the gas passageway 22 (first electrode) and the connector end of the tubular member 26 (second electrode) and an external measurement device 48. The measurement device 48 is of a type well known to those of ordinary skill in the art for using the electric sensing zone method to detect and measure particulates suspended in molten metal. When the probe 10 is inserted into molten metal, the measurement device 48 establishes a current path between the first and second electrodes and passing through the orifice 17 for measuring changes in the electrical potential between the first and second electrodes which are produced by the passage of particulates entrained in the molten metal passing through the orifice 17. Further details concerning the structure and operation of the measurement device 48 are well known to those of ordinary skill in the art and are available from other sources including the above-described patents which are incorporated herein by reference. Accordingly, a detailed discussion of the structure and operation of the measurement device 48 is not necessary for a complete understanding of the present invention.

As best shown in FIG. 3, a liquidus depressing material 50 is provided within the insertion end of the inner tube 16, proximate to the orifice 17. In the presently preferred embodiment, the liquidus depressing material 50 is preferably in the form of a generally helical shaped wire coil. However, it will be appreciated by those of ordinary skill in the art that the liquidus depressing material 50 could be in some other form, such as granular, or could be in some other shape, such as tubular, disk-like or the like. In the presently preferred embodiment, the liquidus depressing material 50 is copper. However, the liquidus depressing material 50 could be of some other suitable material or combination of materials that has the effect of depressing the liquidus temperature of iron or steel. Such materials include Al, Au, Be, C, Co, Ge, Mn, Ni, P, S, Sb, Si and Sn, as well as other individual elements, materials or combination of elements or materials well known to those of ordinary skill in the art. Accordingly, it should be clearly understood that although copper is used in the presently preferred embodiment, the use of copper is only for illustration purposes. As will be appreciated by those of ordinary skill in the art, the liquidus depressing material 50 alloys with the molten metal entering the chamber 15 through the orifice 17 and the resulting alloy has a liquidus temperature which is lower than the liquidus temperature of the molten metal entering the chamber 15. Because the wires 24 are close to the wall of the inner tube 16 the cooling of the liquid metal in the central up-welled area is prevented.

Figure 4:
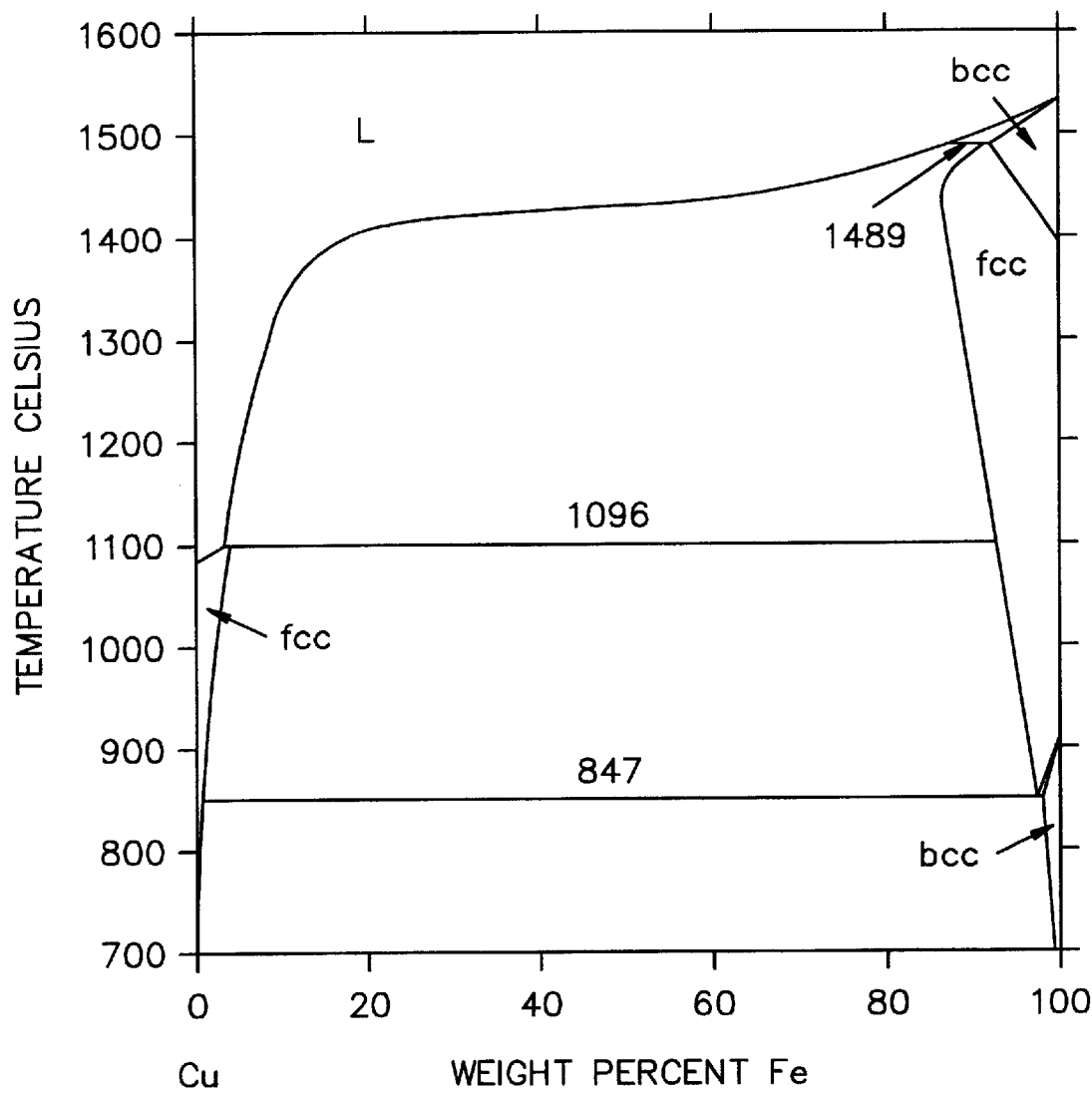
FIG. 4 is a phase diagram which illustrates the effect of the addition of a preferred liquidus depressing material to the chamber of the probe of FIG. 1.

FIG. 4 illustrates the effect of the addition of the copper liquidus depressing material 50 to the chamber 15. For example, in liquid steel containing 0.10% carbon in solution, the liquidus temperature would be approximately 1528° C. and this grade of steel could be continuously cast from a tundish with a temperature of approximately 1570° C. With the present embodiment, approximately 10 g of copper 50 is added to the chamber 15 which when full would contain about 100 g of sampled steel. During immersion of the probe 10 into the molten steel, the copper 50 in the chamber 15 is quickly heated by thermal radiation through the inner tube 16. Looking at the PHASE Diagram of FIG. 4 on the lower horizontal axis of the chart one can find the percentage mixture of iron and copper, pure copper is at the extreme left of the chart and pure iron is on the extreme right. On the vertical axis one can read a temperature that corresponds to a phase event occurring at a given weight percent mixture of copper and iron. Initially with no steel in the chamber 15, the copper would be completely molten in the chamber 15 at about 1085° C. shown by finding the intersections of the liquidus line at 100% copper at the left vertical axis which corresponds to 100% copper. For the purposes of this example, the steel entering the chamber 15 is considered to be 100% iron. Tables and graphs are readily available to those skilled in the art to correct for deviations in the steel from pure iron. After 10 g of molten steel enters the chamber 15, approximating that the 0.1% carbon steel of this example to be essentially 100% Fe, the liquidus temperature for a 50–50 mixture of copper and the steel is found to be slightly above 1425° C. After enough steel has entered the chamber 15 the steel alloys with the copper to lower the percentage of copper to 15%, the liquidus temperature is approximately 1480° C. The addition of copper or another liquidus depressing material 50 lowers the temperature at which the sampled molten metal would normally begin to solidify, thus allowing for more molten metal to be sampled before the chamber 15 freezes. One can appreciate that the depression of the liquidus temperature resulting from alloying in this fashion compensates for the loss of heat by the sampled molten metal to the chamber 15. The proportions of a liquidus depressing material or materials, to the sampled metal is determined by the probe construction, the quantity of material to be sampled and the superheat of the molten metal at the time of sampling. An additional benefit that can be derived from careful selection of the material 50 is that the chemical heat of solution can be exothermic and therefore cause heating of the molten material in the chamber 15 by the action of mixing the molten metal and the liquidus depressing material 50.

In use, the probe 10 is secured to the supporting structure (not shown), so that the first and second electrodes are electrically connected to the measurement device 48 and so that the gas passageway 22 is in fluid communication with the valve 42. Initially, the valve 42 is in the second position, so that an inert purge gas from the purge gas source 46 flows through the gas passageway 22, into the inner tube 16 and out of the orifice 17. The pressure of the inert purge gas is measured, valve 42 is turned off and the rate of inert gas leaking out of orifice 17 is measured as a decrease in pressure over time. The rate of inert gas leaking out of orifice 17 is proportional to the size of the orifice 17. Using the initial pressure and the rate of change of pressure the size of the orifice 17 is calculated for later use. Valve 42 is then returned to the second position. As the probe 10 is inserted through an upper slag layer and into the molten metal, the paper cap 38 is destroyed and the metal slag cap 36 melts to expose the insertion end of the inner tube 16 and the tubular member 26 to the molten metal. As the molten metal engages the inner tube 16, the orifice 17 is effectively sealed causing an increase in gas pressure of the purge gas which is measured by external instrument (not shown). At this time, the valve 42 is changed to the first position, so that the vacuum source 44 is in fluid communication with the gas passageway 22 and the interior of the inner tube 16 to effectively create a vacuum within the chamber 15 thereby, causing the molten metal to flow through the orifice 17 and into the chamber 15. As soon as the molten metal engages the wires 24, a complete electrical circuit is established and the measurement device 48 causes current to flow between the electrodes and passing through the orifice 17 for measuring changes in the electrical potential between the electrodes produced by the passage of particulates entrained in the molten metal as they pass through the orifice 17. The molten metal entering the chamber 15 alloys with the liquidus depressing material 50 for lowering the liquidus temperature of the entering molten metal to thereby permit the detection and measuring process to continue for a longer period of time than would otherwise be permissible without the presence of the liquidus depressing material 50. The detection and measuring process continues until the chamber 15 is filled with liquid metal and the level of the liquid metal effectively blocks the insertion end of the gas passageway 22 to preclude further vacuum pressure in the chamber 15. The blocking method effectively limits more sample material from entering chamber 15 and thus provides a means for creating a predetermined fixed volume of sampled metal without adding additional heat absorbing components. Gas passageway 22 is spaced and thermally isolated from all other components of the probe 10 by the seal member 18 to remain colder than and thus adequately chill the chamber metal upon contact. The duration of the time that the purge gas is fed into the chamber 15 is chosen to allow burn off of the paper cap 38, melting of the slag cap 36 and melting of the liquidus depressing material 50 before the molten metal flows into the chamber 15. It should be appreciated by those of ordinary skill in the art that it is not necessary that all of the liquidus depressing material 50 be melted or completely melted prior to commencement of the inflow of the molten metal through the orifice 17.

It will be appreciated by one of ordinary skill in the art that the particular liquidus depressing material employed and the amount of liquidus depressing material employed will vary to suit a particular application and the chemical conditions of the molten metal to be tested. It will also be appreciate that the size of the chamber 15 and the amount of molten metal entering the chamber 15 can be varied by varying the length of the gas passageway 22 and the length and diameter of the inner tube 16. The liquidus depressing material permits more of the metal to flow through the orifice 17 at a generally continuous rate over the entire measurement cycle to thereby provide a more effective, more accurate measurement of the entrained particulates.

From the foregoing, it will be understood that the present invention comprises an improved probe for detecting and measuring suspended particulates within molten metal. It will be appreciated by those skill in the art that changes could be made to the embodiment described above without departing from the broad inventive concepts thereof. It is understood, therefore, that this invention is not limited to the particular embodiments disclosed, but is intended to cover all modifications within the sphere and scope of the present invention as defined in the appended claims.

We claim:

1. In a probe for insertion into molten metal to detect and measure particulates suspended therein using the electric sensing zone method, the probe comprising:

a sealed inner tube of an electrically insulative material forming a molten metal receiving chamber, the tube including at least one orifice proximate an insertion end of the probe to permit molten metal to flow into the chamber;

a first electrode extending into the chamber for engaging metal within the chamber;

a second electrode surrounding at least a portion of the inner tube for engaging molten metal outside of the chamber, the first and second electrodes being connectable to a measurement device for establishing a current path through the electrodes and passing through the at least one orifice and for measuring changes in the electrical potential between the electrodes produced by the passage of particulates entrained in the molten metal passing through the orifice;

an outer sheath of heat resistant material surrounding at least a portion of the second electrode to provide thermal insulation therefor;

a gas passageway extending out of the inner tube for connection to a vacuum source to create a pressure differential between the inside and outside of the inner tube for facilitating the flow of molten metal through the orifice, wherein the improvement comprises a liquidus depressing material within the chamber for alloying with molten metal entering the chamber to lower the liquidus temperature of the molten metal in the chamber and permit a longer time period for detecting and measuring particulates in the molten metal.

2. The probe as recited in claim 1, where the liquidus depressing material is selected from the group consisting of Al, Au, Be, C, Co, Ge, Mn, Ni, P, S, Sb, Si, Sn and alloys thereof.

3. The probe as recited in claim 1, where in the liquidus depressing material is in the form of a helical shaped wire.

4. The probe as recited in claim 1, wherein the liquidus depressing material melts prior to any molten metal flowing into the chamber.

5. The probe as recited in claim 1, wherein the gas passageway is initially connected to a source of purge gas for causing purge gas to flow into the chamber, at least during insertion of the probe into the molten metal, to prevent molten metal from flowing into the chamber.

6. The probe as recited in claim 5, further comprising a valve for connecting the gas passageway to either the vacuum source or the purge gas source.

7. The probe as recited in claim 1, wherein the gas passageway extends into the inner tube by a predetermined distance to establish the amount of metal which may enter the chamber.

8. The probe as recited in claim 1, wherein the first electrode comprises the gas passageway and at least one wire extending from the gas passageway and into the chamber.

9. The probe as recited in claim 1, wherein the inner dimension of the second electrode is greater than the outer dimension of the inner tube to create an annular space there between.

10. The probe as recited in claim 9, further comprising a spacer member positioned within the annular space proximate the insertion end of the second electrode.

11. In a probe for insertion into molten metal to detect and measure particulates suspended therein using the electric sensing zone method, the probe comprising:

a metal receiving chamber formed of an electrically insulated material, the chamber including an orifice to permit molten metal to flow therein;

a first electrode extending into the chamber for engaging metal within the chamber;

a second electrode located outside of the chamber for engaging molten metal outside of the chamber, the first and second electrodes being connectable to a measurement device for establishing a current path through the electrodes and passing through the orifice and for measuring changes in the electrical potential between the electrodes produced by the passage of particulates entrained in molten metal passing through the orifice and into the chamber;

wherein the improvement comprises a liquidus depressing material within the chamber for alloying with molten metal entering the chamber to lower the liquidus temperature of the molten metal in the chamber and permit a longer time period for detecting and measuring particulates in the molten metal.

12. A method for detecting and measuring particulates suspended in molten metal using a probe including a sealed inner tube of electrically insulated material for establishing a receiving chamber, the tube including an orifice to permit molten metal to flow into the chamber, a first electrode extending into the chamber for engaging molten metal within the chamber, a second electrode surrounding at least a portion of the inner tube for engaging molten metal outside of the chamber, an outer sheath of heat resistant material surrounding at least a portion of the second electrode to provide thermal insulation therefor, and a gas passageway extending out of the inner tube, the method comprising the steps of installing a liquidus depressing material within the chamber;

connecting the first and second electrodes to a measurement device;

connecting the gas passageway to a vacuum source;

installing the probe in molten metal such that molten metal flows through the orifice and into the chamber;

the measurement device establishing a current path through the electrodes and passing through the orifice; and measuring changes in the electrical potential between the electrodes produced by the passage of particulates entrained in the molten metal passing through the orifice.

* * * * *